United States Patent [19]
Elliott et al.

[11] 4,051,053
[45] Sept. 27, 1977

[54] HYDRAULIC FLUIDS COMPRISING ORTHOSILICATE ESTERS

[75] Inventors: John Scotchford Elliott; Gerald John Joseph Jayne; Herbert Frank Askew; Colin John Harrington, all of Swindon, England

[73] Assignee: Castrol Limited, England

[21] Appl. No.: 679,440

[22] Filed: Apr. 22, 1976

Related U.S. Application Data

[63] Continuation of Ser. No. 431,889, Jan. 9, 1974, abandoned.

[30] Foreign Application Priority Data

Jan. 10, 1973 United Kingdom ............ 01409/73

[51] Int. Cl.² .......................... C07F 7/04; C09K 3/00
[52] U.S. Cl. .............................. 252/78.3; 260/448.8 R
[58] Field of Search ................. 260/448.8 R; 252/78.3

[56] References Cited

U.S. PATENT DOCUMENTS

| | | | |
|---|---|---|---|
| 3,308,149 | 3/1967 | Schenck et al. | 260/448.8 R |
| 3,320,297 | 5/1967 | Pino et al. | 260/448.8 R |
| 3,806,549 | 4/1974 | Foley | 260/448.8 R |

FOREIGN PATENT DOCUMENTS 1,075,236  7/1967  United Kingdom

OTHER PUBLICATIONS

Emblem et al., J. Inorg. Nucl. Chem., 30, 721-727 (1968).

*Primary Examiner*—J.C. Cannon
*Attorney, Agent, or Firm*—Bacon & Thomas

[57] ABSTRACT

As novel compounds, orthosilicate esters having the general formula:

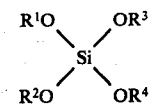

wherein $R^1$ is a propylene glycol monoalkyl ether residue containing from 1 to 8 carbon atoms in the terminal alkyl group or is a tertiary alkyl group; each of $R^2$, $R^3$ and $R^4$ is the same or different and is an ethylene or propylene glycol monoalkyl ether residue containing from 1 to 8 carbon atoms in the terminal alkyl group or is a tertiary alkyl group, provided that when $R^1$ is a propylene glycol monoalkyl ether residue each of $R^2$, $R^3$ and $R^4$ are also propylene glycol monoalkyl ether residues; the total number of carbon atoms in $R^1$, $R^2$, $R^3$, and $R^4$ being at least 15 and at least one of $R^1$, $R^2$, $R^3$, and $R^4$ being a glycol monoalkyl ether residue.

Also disclosed are hydraulic fluids containing the novel compounds.

13 Claims, No Drawings

HYDRAULIC FLUIDS COMPRISING ORTHOSILICATE ESTERS

This is a continuation of application Ser. No. 431,889, filed Jan. 9, 1974 and now abandoned.

This invention relates to novel compounds, suitable for use in hydraulic fluids, more particularly to certain new orthosilicate esters suitable for use in hydraulic fluids.

Hydraulic fluids are commonly used in hydraulic systems performing various different functions and the combination of properties required of the fluid varies from case to case. One of the severest requirements is the case of automotive brake and clutch fluids. Vehicle manufacturers and other authorities lay down very stringent specifications for such fluids, requiring very high standards with respect to numerous properties.

Recently, there has emerged a growing tendency in vehicle design to use a single hydraulic system to operate equipment, such as power-steering, shock absorbers and brakes, which hitherto were provided with separate hydraulic systems. This has created serious problems in the formulation of suitable fluids. The mineral oil based fluids hitherto used in power-steering systems and shock absorbers are satisfactory with respect to the nitrile and chloroprene rubber used for the seals and gaskets in such systems but are highly detrimental to the natural and synthetic rubbers used in the construction of hydraulic brake and clutch systems. This results in excessive swelling of the latter seals which can lead to a serious malfunction of the brake or clutch system. Conversely, the fluids hitherto used in brake and clutch systems, which are normally based on glycols, glycol ethers and/or glycol ether esters, and which have operated satisfactorily in such systems, have a detrimental effect on the nitrile and chloroprene rubber gaskets used in power-steering systems and shock absorbers which can also lead to malfunctioning. In the case of vehicle operation the characteristic of reliability in operation, which is generally desirable in all mechanical devices, is increased in importance to an absolutely essential requirement by virtue of safety considerations. The need has therefore arisen for a fluid which can be used satisfactorily in a central system controlling the operation of a number of different items of equipment.

Among the many varied types of fluids which have been proposed as base stocks for hydraulic fluids are certain orthosilicate esters. These have been proposed, and in some cases used, for certain categories of hydraulic fluid wherein hydrolytic stability is of comparatively low importance. However, such esters have been consistently rejected by manufacturers for fluids to be used for automotive purposes because of the totally inadequate hydrolytic stability for such purposes. We have now found certain novel orthosilicate esters having superior hydrolytic stability which, by virtue of their good balance of required properties such as boiling point, hydrolytic stability and rubber swell properties, are suitable for use in the formulation of hydraulic fluids for automotive equipment including central system fluids. These orthosilicate esters are characterised by the presence of at least one glycol monoether residue and at least one branched chain organic group (which in some cases may be the glycol monoether residue).

Accordingly, the present invention provides an orthosilicate ester having the general formula:-

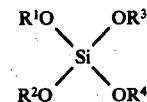

wherein $R^1$ is a propylene glycol monoalkyl ether residue containing from 1 to 8 carbon atoms in the terminal alkyl group or is a tertiary alkyl group; each of $R^2$, $R^3$ and $R^4$ is the same or different and is an ethylene or propylene glycol monoalkyl ether residue containing from 1 to 8 carbon atoms in the terminal alkyl group or is a tertiary alkyl group, provided that when $R^1$ is a propylene glycol monoalkyl ether residue each of $R^2$, $R^3$ and $R^4$ are also propylene glycol monoalkyl ether residues; the total number of carbon atoms in $R^1$, $R^2$, $R^3$ and $R^4$ being at least 15 and at least one of $R^1$, $R^2$, $R^3$ and $R^4$ being a glycol monoalkyl ether residue.

The term "tertiary alkyl group" as employed herein is to be understood to mean an alkyl group containing a tertiary carbon atom, i.e. a carbon atom having no hydrogen atom substituted thereon.

The glycol monoalkyl ether residues present in the orthosilicate esters of the present invention are derived from monoalkyl ethers of glycols which may be mono-, di- or poly-glycols and such monoalkyl esters can be represented by the formula:-

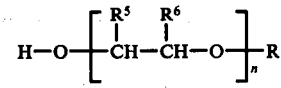

wherein each of the $R^5$ and $R^6$ is a hydrogen atom or methyl group, provided that $R^5$ and $R^6$ are not both methyl groups; R is an alkyl group containing from 1 to 8 carbon atoms; and n is an integer. Thus, the residues of such glycol monoalkyl ethers can be represented as:-

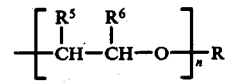

It is preferred that R contains from 1 to 4, most preferably 1 or 2, carbon atoms. The integer n is 1 in the case of a mono-glycol monoether, 2 in the case of a di-glycol monoether and 3 or more in the case of a poly-glycol monoether. In general the larger the molecule of the orthosilicate ester the higher the boiling point and the carbon atom content of the orthosilicate ester molecule is a convenient indication of its size. Accordingly, a minimum carbon atom content of 15 is required to provide a compound of sufficiently high boiling point and such content will depend, inter alia, on the integer $n$. It is preferred therefore that n is at least 2 and it may be as high as 20, more preferably not more than 6. In general $n$ is most preferably from 2 to 4. However, it is to be understood that, for example, it is also possible for n to be 1 in some glycol monoether residues and to be counter-balanced by n being much larger in other residues. As hereinbefore indicated, total carbon atom content is a convenient indicator of molecular size, i.e. the cumulative effect of the value of each integer n plus the size of any alkyl groups constituting $R^1$, $R^2$, $R^3$ and/or $R^4$, and the total carbon atom content will normally be in the range of 15 to 120, more preferably 15 to 60.

As hereinbefore indicated $R^1$ may, alternatively, be a tertiary alkyl group and in this case $R^1$ preferably contains 4 to 10, more preferably 4 to 8, carbon atoms. As also hereinbefore indicated any of $R^2$, $R^3$ or $R^4$ may be a tertiary alkyl group. In this case also any such alkyl groups preferably contain 4 to 10, more preferably 4 to 8 carbom atoms. However, at least one of the groups $R^1$, $R^2$, $R^3$ and $R^4$ must be a glycol monoalkyl ether residue of the type hereinbefore defined and preferably at least 2 of the groups $R^1$, $R^2$, $R^3$ and $R^4$ are glycol monoether residues.

Accordingly, in the two most preferred embodiments of the present invention there are provided orthosilicate esters having the general formula:-

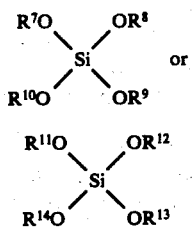

In the case of formula (A):-
i. Each of $R^7$, $R^8$, $R^9$ and $R^{10}$ is the same or different; and
ii. Each of $R^7$, $R^8$, $R^9$ and $R^{10}$ is a propylene glycol monoalkyl ether residue of the formula:-

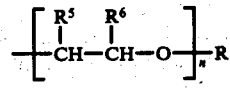

in which:-
a. in each adjacent $R^5$ and $R^6$ one is a hydrogen atom and the other is a methyl group;
b. each n is the same or different and the total value of all integers n is from 8 to 16, especially wherein each n is from 2 to 4; and
c. each R is the same or different and is a methyl or ethyl group.

In the case of orthosilicate esters of foregoing formula (B):-
i. $R^{11}$ is a tertiary alkyl group containing 4 to 8 carbon atoms, particularly a tertiary butyl group;
ii. $R^{12}$ is a glycol monoalkyl ether residue of the formula

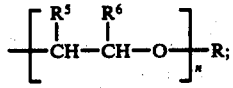

iii. $R^{13}$ is the same as or different from $R^{12}$ and is a glycol monoalkyl ether residue of the formula

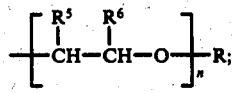

iv. $R^{14}$ is a tertiary alkyl group containing 4 to 8 carbon atoms, particularly, a tertiary butyl group, and $R^{14}$ is the same as or different from $R^{11}$ or $R^{14}$ is a glycol monoalkyl ether residue of the formula

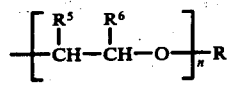

and is the same as either $R^{12}$ or $R^{13}$ or is different from both $R^{12}$ and $R^{13}$; and
v. In glycol monoalkyl ether residues of the formula

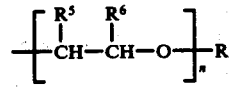

a. each $R^5$ and $R^6$ is the same or different and both are hydrogen atoms or in each adjacent $R^5$ and $R^6$ one is a hydrogen atom and the other is a methyl group;
b. each n is the same or different and the total value of all integers n is from 4 to 8 when $R^{14}$ is a branched chain alkyl group or from 6 to 12 when $R^{14}$ is a glycol monoalkyl ether residue, it being especially preferred that each n is from 2 to 4; and
c. each R is the same or different and is a methyl or ethyl group.

The orthosilicate esters of the present invention are useful hydraulic fluid components and for this purpose they may be used as the base-stock. In this case the orthosilicate esters will constitute all, or substantially all, of the hydraulic fluid, e.g. 70% or 99% by weight. When used in this manner the orthosilicate esters may, if desired, be blended with small quantities of other known base stocks.

However, the orthosilicate esters are particularly useful for blending with substantial quantities of other known base-stocks to modify the properties of the latter or to provide a fluid with a blend of the properties of the separate components. In this case the orthosilicate esters may be present in a wide range of proportions, e.g. from 1% to 70% by weight, but more preferably 10% to 60% by weight. In this way one may for example, formulate central systems fluids combining in large measure the good rubber swell properties in respect of nitrile rubber of the orthosilicate esters and the good rubber swell properties, in respect of natural rubber and synthetic rubbers commonly used in automotive brake and clutch systems, of known synthetic base-stocks for brake and clutch systems.

Among the base-stocks with which the orthosilicate esters of the present invention may be blended are the well-known and widely used glycols, polyoxyalkylene glycols and mono- and di- alkyl esters thereof. Such materials are commercially available, for example under the Registered Trade Mark "Ucon". Other examples of these materials are those available under the trade names "Oxitol" and "Cellosolve". Other base-stocks are the borate esters of U.K. Pat. Specification No. 1341901. Further examples of known base-stocks which may be blended with the orthosilicate esters of the present invention are the dicarboxylic acid esters and glycol di-esters referred to in U.K. Pat. Specification No. 1341901 and more fully described in U.K. Pat. Specification Nos. 1083324 and 1249803 respectively.

The present invention, in one of its aspects, includes hydraulic fluids containing at least 70% of an orthosilicate ester of the present invention, or a mixture of such esters, or a blend of one of more orthosilicate esters of the present invention with one or more known hydraulic fluid base-stocks.

It is highly desirable that the hydraulic fluids of the present invention have a kinematic viscosity at −40° C of not more than 5,000cSt., especially not more than 2,000cSt., and a boiling point of at least 230° C., especially at least 260° C.

In use the hydraulic fluids of the present invention will normally be blended with small quantities of various additives of the type commonly employed in hydraulic fluids.

Typical additives which may be used in the invention are lubricity additives selected from castor oil or castor oil treated in various ways, for example, Firsts Castor Oil
Castor Oil to Specification DTD72
Blown Castor Oil, i.e. castor oil blown with air or oxygen while being heated.
Special Pale Blown Castor Oil, i.e. a similarly blown castor oil.
"Hydricin 4", i.e. a commercially available ethylene oxide/propylene oxide treated castor oil.

Other lubricity additives which may be incorporated in hydraulic fluids in accordance with the present invention include borate esters, e.g., tricresyl borate and phosphorus-containing esters, especially phosphates, e.g. tricresyl phosphate.

The hydraulic fluids of the present invention may also include minor proportions of polyoxyalkylene glycols or ethers thereof, e.g. those sold by Union Carbide Corporation under the Registered Trade Mark "Ucon", particularly those of the LB and HB series. Suitable examples of these polyoxyalkylene glycols and their ethers and esters are given in British Pat. Specification No. 1,055,641. Other suitable lubricity agents are orthophosphate or sulphate salts of primary or secondary aliphatic amines having a total of from 4 to 24 carbon atoms, dialkyl citrates having an average of from 3½ to 13 carbon atoms in the alkyl groups, aliphatic dicarboxylic acids and esters thereof, specific examples being Diamylamine orthophosphate
Dinonylamine orthophosphate
Diamylamine sulphate
Dinonyl citrate
Di(2ethyl hexyl) citrate
Polyoxyethylene sebacate derived from a polyoxyethylene glycol of M.W. 200
Polyoxyethylene adipate derived from polyoxyethylene glycol of M.W. 200
Polyoxyethylene azelate derived from a polyoxyethylene glycol of M.W. 200
Polyoxyethylene/polyoxypropylene glutarate derived from mixed polyoxyglycols of average M.W. of about 200
Glutaric acid
Azelaic acid
Sebacic acid
Succinic acid
Di ethyl sebacate
Di 2-ethyl hexyl sebacate
Di iso octyl azelate Unsaturated aliphatic acids or their salts may also be used, e.g. oleic acid or potassium ricinoleate.

Corrosion inhibitors which may be used in the present invention may be selected from heterocyclic nitrogen containing compounds, e.g. benzotriazole and benzotriazole derivatives such as those described in British Patent Specification No. 1,061,904 or mercapto benzothiazole. Many amines or derivatives thereof are also suitable as corrosion inhibitors, for example di n-butylamine
di n-amylamine
cyclohexylamine
morpholine
triethanolamine and soluble salts thereof, e.g. cyclohexylamine carbonate.

Phosphites are also good corrosion inhibitors, e.g.
Tri phenyl phosphite
Di isopropyl phosphite and certain inorganic salts may be incorporated, e.g. sodium nitrate.

Other additives which may be included are antioxidants such as diarylamines, e.g. diphenylamine, p,p'-dioctyl-diphenylamine, phenyl-α-naphthylamine or phenyl-β-naphthylamine. Other suitable antioxidants are those commonly known as hindered phenols which are exemplified by 2,4-dimethyl 6-t-butyl phenol
2,6-di-t-butyl-4-methyl phenol
2,6-di-t-butyl phenol
1,1-bis (3,5-di-t-butyl-4-hydroxyphenyl)-methane
3,3',5,5',-tetra-t-butyl - 4 - 4' - dihydroxy-diphenyl
3-methyl-4, 6-di-t-butyl phenol
4-methyl-2-t-butyl phenol Yet further additives which may be used are phenothiazine and its derivatives, for example those having alkyl, or aryl, groups attached to the nitrogen atom or to the aryl groups of the molecule.

Other additives which may be used include alkylene oxide/ammonia condensation products as corrosion inhibitor, for example the propylene oxide/ammonia condensation product described in U.K. Patent Specification No. 1,249,803. Further lubricity additives which may be used are complex esters, such as that sold under the trade name "Reoplex 641" and also described in Specification No. 1,249,803. Moreover, long chain (e.g. $C_{10-18}$) primary amine corrosion inhibitors and polymerised quinoline resin antioxidants, as described in Specification No. 1,249,803, may be used, examples of such amines and resins being the commercially available materials Armeen 12D and Agerite resin D respectively.

Conventional additives such as those hereinbefore described are normally employed in small amounts such as 0.05% to 10% for example, 0.1% to 2% by weight.

The orthosilicate esters of the present invention may be prepared by the techniques conventionally employed in the preparation of such esters, examples of which are the reaction of a silicon tetrahalide such as Si Cl$_4$ with four parts of hydroxy compound such as glycol monoether or alkanol or the transesterification of a tetra (hydrocarbyl) silicate with the appropriate quantities of a hydroxy compound. For example, to prepare an orthosilicate ester containing four identical glycol monoether residues silicon tetrachloride can be reacted with a glycol monoether in 1:4 molar ratio or a tetra (hydrocarbyl) silicate can be transesterified with a glycol monoether in 1:4 molar ratio but preferably this reaction or transesterification is carried out in the presence of an excess of glycol monoether, e.g. about 10% excess in the case of reaction with Si Cl$_4$ or a larger excess in the case of a transesterification reaction.

To prepare an orthosilicate ester containing 2 residues of one glycol monoether plus 2 residues of a different glycol monoether a sequential procedure can be followed, i.e. reaction with Si Cl₄ in 2:1 molar ratio or transesterification in 2:1 molar ratio followed by further reaction or transesterification with a different glycol monoether in 2:1 molar ratio. Thus the nature of the glycol monoether residues is determined by selection of the glycol monoether used and the number of each species of residue is determined by the molar ratio used. Examples of suitable tetra (hydrocarbyl) silicates are tetramethyl silicate, tetraphenyl silicate and tetraethyl silicate, the last being especially preferred. Other suitable tetra (hydrocarbyl) silicates are described in U.K. Patent Specification No. 1,075,236.

In the case of orthosilicate esters containing one or more alkyl groups in place of glycol monoether residues, the same preparative techniques can be used except in that part of the glycol monoether is replaced by the appropriate alkanol. In this case it is preferred to introduce the alkyl group before the glycol monoether residues, for example by reaction of Si Cl₄ with an alkanol such as t-butanol in the quantity required to provide the desired number of alkyl groups followed by reaction with glycol monoether. When preparing orthosilicate esters containing alkyl groups by transesterification a suitable tetra (alkyl) silicate, e.g. tetra (t-butyl) silicate, containing the desired alkyl group(s), can be reacted with a glycol monoether in 1:1, 1:2 or 1:3 molar ratio to introduce 1,2 or 3 glycol monoether residues respectively. Alternatively, and preferably a tetra (hydrocarbyl) silicate such as tetraethyl silicate can transesterified with an appropriate alcohol to introduce the desired number of the required alkyl groups and the compound so formed transesterified with glycol monoether to replace the remaining ethyl groups with glycol monoether residues.

When preparation of the orthosilicate esters is by transesterification, the tetra (hydrocarbyl) silicate starting material and the reaction conditions may be chosen so that liberated hydroxy compounds can be removed from the reaction mixture by distillation. For example, transesterification of tetraethyl silicate with glycol monoether yields ethanol as well as tetra (glycol monoether) orthosilicate. The comparatively low boiling ethanol can be stripped off so that the transesterification, which is an equilibrium reaction, can proceed to completion.

In a preferred preparation of the novel orthosilicate esters by the transesterification route a catalyst is used, for example, sodium metal which facilitates the reaction via formation of the alkoxide of the glycol monoether or known transesterification catalysts such as p-toluene sulphonic acid or a tetraalkyl, e.g. tetraisopropyl, titanate.

Preparation of the othosilicate esters of the present invention from a silicon tetrahalide may be readily carried out by reaction of the appropriate hydroxy compound with the tetrahalide at a temperature of from −40° C to 150° C, preferably 40° C to 100° C. If desired this reaction may be carried out in the presence of an inert solvent such as alkyl ethers, toluene, petroleum ether, etc. In addition an acid acceptor, such as a tertiary amine may be used to neutralise hydrogen halide formed in the reaction.

When preparation is by the transesterified route the reaction temperature employed may be, for example, 80° C to 250° C, preferably 120° C to 200° C and likewise an inert solvent may be used if desired. Further details of the manner in which glycol monoether orthosilicates may be prepared are given in Journal of Inorganic Nuclear Chemistry, 1968, Volume 30, pages 721 to 727.

The invention will now be illustrated with reference to the following examples:

Preparation of Tris(triethylene glycol monomethyl ether) t-butyl silicate

Example 1

Preparation of Tris(triethylene glycol monoethyl ether)t-butyl silicate

| Reactants | Mol. Wt. | Amount Taken | No. of Moles |
|---|---|---|---|
| Silicon tetrachloride | 170 | 170 g | 1.0 |
| Tertiary butanol | 74 | 74 g | 1.0 |
| Triethylene glycol monomethyl ether | 164 | 492 g | 3.0 |
| Diethyl ether | | 600 ml | |
| Pyridine | | 85 g | |

The silicon tetrachloride and diethyl ether were placed in a 2-liter, round-bottomed, three-necked flask fitted with a stirrer, thermometer, thermocouple, nitrogen inlet, dropping funnel, condenser and water column with traps. The tertiary butanol and pyridine (the latter being used as an acid acceptor to prevent reaction of tertiary butanol with hydrogen chloride produced in the reaction) were placed in the dropping funnel and added slowly to the flask at an initial temperature of 20° C. Temperature was recorded by the thermocouple due to the thermometer being obscured by a white precipitate. The addition of the tertiary butanol was completed over a period of 1½ hours during which the temperature was allowed to rise as a result of the exothermic reaction, to a maximum of 35° C at the end of the addition. The reaction mixture was then stirred for a further ½ hour at room temperature and then filtered.

The apparatus was reassembled as before and the filtered reaction mixture placed in the flask. The triethylene glycol was then added to the reaction mixture via the dropping funnel, slowly at first which gave no detectable exotherm so the rate of addition was increased to give an exotherm of 5° C (max.). During the addition nitrogen was blown in stringly to remove hydrogen chloride.

The crude product was then heated to 70° C for a total of 9½ hours to ensure completion of the reaction and finally stripped to 170° C at a pressure of 0.05 mm. Hg to yield 140g (23.7% by weight based on the silicon tetrachloride) of a clear, brown liquid containing 4.95% Si by weight (theory 4.75%) and 0.17% by weight residual chlorine (theory 0%).

Example 2

Preparation of Tris(triethylene glycol monoethyl ether)t-butyl silicate

| Reactants | Mol. Wt. | Amount Taken | No. of Moles |
|---|---|---|---|
| Silicon tetrachloride | 170 | 170 g | 1.0 |
| Tertiary butanol | 74 | 74 g | 1.0 |
| Triethylene glycol monomethyl ether | 164 | 542 g | 3.3 |
| Pyridine | 79g | 347 g | 4.4 |
| Toluene | | 1800 ml | |

The silicon tetrachloride and 250 ml toluene were placed in a two-liter, round-bottomed, three-necked flask, fitted with a dropping funnel, stirrer, condenser, nitrogen inlet and thermocouple. The flask was placed on an ice bath and 87g pyridine added to the flask over a period of 40 minutes during which the temperature of the flask contents was maintained at 15° C±1° C. Thereafter the flask was removed from the ice bath and stirred for 15 minutes during which its temperature was allowed to rise to ambient (about 20° C). The tertiary butanol, dissolved in 50ml toluene, was then added to the flask over a period of ½ hour during which the temperature was maintained in the range 20° C to 25° C. The contents of the flask were then heated to 80° C for 1½ hours.

The contents of the flask were then poured into a larger (3-liter) flask similarly equipped to the original reaction vessel and a further 500 ml toluene added. Thereafter the remaining pyridine (260g) was added over a period of 1½ hours during which the temperature was maintained in the range 20° C to 25° C. The triethylene glycol monomethyl ether was then added slowly to the reaction mixture. Over a period of three-fourths hour one-third of the glycol ether was added with the temperature maintained in the range 20° C to 35° C. At this the flask contents became too thick for further reaction and addition was stopped while a further 600 ml toluene was added. Addition of the glycol ether was then resumed and the remainder added at a temperature maintained in the range of 30° C to 40° C, the addition being finally completed in a total of 2½ hours with the remaining quantity of toluene (400ml) being added after three-fourths of the glycol ether had been added. The reaction mixture was then stirred at 90° to 100° C for 2½ hours and then a further 7 hours at 80° C. Finally, the crude product was filtered, using a diatomaceous filter aid, stripped on a rotary evaporator and finally stripped to a temperature of 170° C under a pressure of 0.4 to 0.5mm. Hg to yield 236g (40% by weight based on the silicon tetrachloride) of a deep yellow liquid containing 4.86% Si by weight (theory 4.75%) and 0.05% by weight residual chlorine (theory 0%).

Example 3

Tris(tripropylene glycol monomethyl ether)neopentyl silicate

| Reactants | |
|---|---|
| Silicon tetrachloride | 174 g |
| Tripropylene glycol monomethyl ether (commercially available material marketed under the trade name "DOWANOL TPM" | 679 g |
| Neopentyl alcohol | 88 g |
| Pyridine | 340 g |
| Toluene | 2.5 liters |

The toluene and silicon tetrachloride were mixed in a 5 liter flask and a mixture of the neopentyl alcohol and 79g pyridine added with cooling, during which the reaction temperature reached a maximum of 42° C due to the exothermic reaction taking place. The reaction mixture was heated to 100° C for 4 hours and then allowed to cool overnight. Thereafter the tripropylene glycol monomethyl ether and the remainder of the pyridine was added over a period of ½ hour during which the resulting exotherm was controlled by cooling (water-bath). The reaction mixture was then heated to 112° – 114° C for 5 hours 20 minutes, cooled and the precipitated pyridine hydrochloride filtered off. The solvent was then stripped off on a rotary evaporator and the product finally stripped under high vacuum (200° C/0.1mm Hg). to yield 484.4g (66.3%) of the final product. Analysis:- 3.74% Si (theory 3.84%) residual chlorine 0.15%

Example 4

Tris(tripropylene glycol monomethyl ether) silicate

| Reactants | |
|---|---|
| SiCl₄ | 170 g |
| Tripropylene glycol monomethyl ether (as in Example 3.) | 906 g |
| Pyridine | 348 g |
| Toluene | 2.5 liters + 50 ml + 250 ml |

A mixture of the pyridine and tripropylene glycol monomethyl ether was added, over 1 hour, to the Si Cl₄ dissolved in 2.5 liters toluene during which a water bath was used to keep the temperature below 50° C. During the addition the reaction mixture became more viscous and two 250 ml portions of toluene were added to facilitate stirring. The reaction mixture was then heated to 100° C for 4 hours, cooled, filtered and the solvent stripped off (105° C/20 torr). The resulting product was then stripped under high vacuum (200° C/0.1mm Hg) to yield 676.4g (79.8%) of a pale yellow final product. Analysis:- 3.4% Si (theory 3.3%) residual chlorine 0.11%

Example 5

Tris(triethylene glycol monomethyl ether)t-butyl silicate

| Reactants | |
|---|---|
| SiCl₄ | 170 G |
| t-Butanol | 74 g |
| Triethylene glycol monomethyl ether | 542 g |
| Pyridine | 347 g |
| Toluene | 2.5 liters + 250 ml |

The SiCl₄ and toluene (2.5 liters were mixed and a mixture of the t-butanol and 87g pyridine added thereto, during which the temperature was maintained below 50° C. The reaction mixture was then heated to 100° C for four hours, cooled and then a mixture of the triethylene glycol monomethyl ether and the remainder of the pyridine added (during which the temperature was maintained below 50° C). Further toluene (250 ml) was added to facilitate stirring and the reaction mixture was then heated to 100° C for a total of 4 hours, cooled, filtered and toluene stripped off (100° C/20 torr.) The resulting product was then stripped under high vacuum (210° C/0.5mm Hg) to yield 346g (70.4%) of the final product. Analysis:- 4.92% Si (theory 5.68%) residual chlorine 0.04%

Example 6

Bis(dipropylene glycol monomethyl ether)bis(t-butyl) silicate

| Reactants | |
|---|---|
| SiCl₄ | 170 g |
| Dipropylene glycol monomethyl ether (commercially available material marked under the trade name "DOWANOL DPM") | 326 g |
| t-Butenol | 148 g |
| Pyridine | 348 g |
| Toluene | 2.5 liters |

The Si Cl₄ and toluene were mixed and then a mixture of the t-butanol and 174g pyridine added thereto over a period of 2 hours during which an exotherm was controlled so that the temperature of the reactants did not exceed 41° C. The reaction mixture was heated to 100° C for 4 hours, allowed to cool and then a mixture of the dipropylene glycol monomethyl ether and the remainder of the pyridine added thereto. The resulting mixture was heated to 100° C for 4 hours, cooled, filtered, toluene stripped off, refiltered and finally stripped under high vacuum (180° C/0.01mm Hg.) to yield 248.2g (53%) of the final product as a clear yellow liquid. Analysis:- 6.02% Si (theory 5.98%) residual chlorine 0.36%

Example 7

| Bis(t-butyl)(dipropylene glycol monomethyl ether) (triethylene glycol monomethyl ether) silicate | |
|---|---|
| Reactants | |
| SiCl$_4$ | 170 g |
| t-Butanol | 148 g |
| Dipropylene glycol monomethyl ether ("DOWANOL DPM") | 148 g |
| Triethylene glycol monomethyl ether | 197 g |
| Toluene | 2.5 liters |
| Pyridine | 332 g |

A mixture of the t-butanol and pyridine (158g) was added to the toluene and Si Cl$_4$ previously mixed in a 5-liter flask (with water bath cooling to maintain temperature below 50° C). The reactants were then heated to between 80° C and 100° C for 4 hours, allowed to cool and a mixture of the dipropylene glycol monomethyl ether and pyridine (79g) was added thereto (very little exotherm). The reaction mixture was then heated to 80° C for 4 hours, allowed to cool and a mixture of the triethylene glycol monomethyl ether and the remainder of the pyridine (95g) was added thereto (with water bath cooling). Thereafter the reaction mixture was heated to 100–104° C for 6 hours, allowed to cool, filtered, toluene stripped off and stripped under high vacuum (180° C/0.05mm Hg.). The resulting product was filtered to yield 413.1g (86%) of a clear yellow liquid. Analysis:- 5.85% Si (theory 5.78%) residual chlorine 0.24%

Example 8

| Tris(dipropylene glycol monomethyl ether)t-butyl silicate | |
|---|---|
| Reactants | |
| Si Cl$_4$ | 170 g |
| t-Butanol | 74 g |
| Dipropylene glycol monomethyl ether ("DOWANOL DPM") | 488 g |
| Pyridine | 348 g |
| Toluene | 1 liter + 200 ml + 200 ml + 200 ml + 400 ml + 1 liter |

The t-butanol and pyridine 80g were mixed and added to a previously prepared mixture of the Si Cl$_4$ and toluene (1 liter). During the addition water bath cooling was used to control the resulting exotherm. Thereafter the reactants were heated to 80° C for 3 hours. The remainder of the pyridine and the dipropylene glycol monomethyl ether were mixed and then added to the reaction mixture. During this addition the reaction mixture became viscous and difficult to stir and further portions of toluene (3 × 200 ml and then 1 × 400ml) were added as necessary. The exotherm during the addition was controlled by water bath cooling. Following the addition the reaction mixture was transferred to a 5 liter flask using a further 1 liter of toluene and then heated to 80° C for 12 hours. The resulting product was filtered, the solvent stripped off and the product stripped under high vacuum (200° C/0.1mm Hg.). Finally the product was refiltered to yield 399g (73.6%) of clear yellow liquid. Analysis:- 5.48% Si (theory 5.17%) residual chlorine 0.15%

Example 9

| Bis(triethylene glycol monomethyl ether(bis (t-butyl)silicate | |
|---|---|
| Reactants | |
| SiCl$_4$ | 170 g |
| t-Butanol | 148 g |
| Triethylene glycol monomethyl ether | 361 g |
| Pyridine | 348 g |
| Toluene | 2.5 liters + 250 ml |

A mixture of the t-butanol and pyridine (174g) was added to a previously prepared mixture and the Si Cl$_4$ and toluene (2.5 liters), the temperature being maintained below 50° C during the addition. The reaction mixture was heated to 100° C for 4 hours, cooled and a mixture of the triethylene glycol monomethyl ether and the remainder of the pyridine added thereto. A slight exotherm resulted and the temperature was maintained below 50° C. The reaction mixture was then heated to 100° C four 4 hours during which time a further 250 ml toluene was added to render stirring easier. The resulting crude product was cooled, filtered, toluene stripped off, then stripped under high vacuum to yield 323.1g (64.6%) of the final product as a clear, pale yellow liquid. Analysis:- 5.7% Si (theory 5.6%) residual chlorine 0.05%.

Example 10

| Bis(tripropylene glycol monomethyl ether)bis(t-butyl)silicate | |
|---|---|
| Reactants | |
| SiCl$_4$ | 170 g |
| t-Butanol | 148 g |
| Tripropylene glycol monomethyl ether ("DOWANOL TPM") | 453 g |
| Pyridine | 348 g |
| Toluene | 2.5 liters |

A mixture of t-butanol and pyridine (174g) was added to a mixture of the Si Cl$_4$ and the toluene, with water bath cooling, over a period of 2 hours during which the temperature of the reactants rose to 38° C (max.) due to a moderate exotherm. The reactants were then heated to 100° C for 4 hours, cooled and then a mixture of the tripropylene glycol monomethyl ether and the remaining pyridine was added thereto over a period of 2 hours (during which a small exotherm raised the temperature of the reaction mixture to a maximum of 30° C). The reaction mixture was then heated to 100° C for 4 hours, cooled, filtered, solvent stripped off and the product finally stripped under high vacuum (180° C/0.1mm. Hg.) to yield 367.2g (63%) of the final product. Analysis: 4.96% Si (theory 4.8%) residual chlorine not measured

Example 11

| Tris (tripropylene glycol monomethyl ether) t-butyl slicate | |
|---|---|
| reactants | |
| SiCl$_4$ | 119 g |
| t-Butanol | 51.8 g |
| Tripropylene glycol monomethyl ether ("DOWANOL TPM") | 474 g |
| Pyridine | 237 g |
| Toluene | 250 ml + 300 ml + 600 ml + 200 ml |

A mixture of the t-butanol and 80g pyridine was added to a mixture of the Si Cl$_4$ and toluene (250ml) in a flask fitted with a water bath for cooling. The resulting exotherm raised the temperature to 30° C. A further 300 ml toluene was added to maintain fluidity and the reaction mixture was then refluxed for 2 hours. The reaction mixture was then cooled and a mixture of the tripropylene glycol monomethyl ether and the remaining pyridine was added over a period of 1 hour during which little exotherm was noticed. A further 600ml toluene was also added. The reaction mixture was heated to 90° C for 10 hours after transferring to a larger flask with the aid of a further 200ml toluene. The crude product was worked up by filtering, stripping off the solvent on a rotary evaporator and finally stripping under high vacuum (180° C/0.1mm Hg.) to yield 380g (75.9%) of the final product as a light yellow liquid. Analysis:- 3.86% Si (theory 3.91%) residual chlorine 0.76%

Example 12

| Tetra (dipropylene glycol monomethyl ether) silicate | |
|---|---|
| Reactants | |
| SiCl$_4$ | 170 g |
| Dipropylene glycol monomethyl ether ("DOWANOL DPM") | 650 g |
| Pyridine | 348 g |
| Toluene | 2.5 liters |

The dipropylene glycol monomethyl ether and pyridine were mixed together and added to the previously mixed Si Cl$_4$ and toluene (with exotherm to a maximum temperature of 38° C). The reaction mixture was then heated to 100° C for 3½ hours, cooled on a water bath, filtered to remove pyridine hydrochloride and the solvent stripped off on a rotary evaporator at 100° C/20 torr. The crude product was then stripped under high vacuum (180° C/0.1 torr) and filtered twice to yield 152g (20.5%) of a clear golden liquid. Analysis:- 5.0% Si (theory 5.43%) residual chlorine 0.05%

Infra-red spectra of the products of all of the foregoing Examples 1 to 12 were consistent with the expected product having been obtained in each case.

The suitability of orthosilicate esters of the present invention for use in hydraulic fluids was demonstrated by measuring the Reflux Boiling Point, Hydrolytic Stability and Rubber Swelling Effect of various esters. Reflux Boiling point was measured in the manner specified by the SAE J1703c specification. Rubber Swell was measured by placing a rubber square (approximately 1 × 1 × (1/10inches) in a 2-ounce bottle provided with a layer of glass beads at the bottom. The bottle was then filled with the test fluid and placed in an oven for 3 days at a constant temperature, whereafter the rubber square was removed, washed with ethanol and dried. The volume of the rubber square was accurately measured before and after the test by the well known displacement method and the percentage volume increase calculated. In this manner styrene-butadiene rubber squares were used at 120° C and natural rubber squares, being more temperature-sensitive, at 70° C, these being the usual temperatures at which to carry out these tests. In addition nitrile and chloroprene rubber squares were also used and in these cases a temperature of 70° C was used, there being no established practice in this respect since hitherto it has not been normal for nitrile and chloroprene rubber to come into contact with brake fluids and hence these rubbers have not been tested in this manner.

Hydrolytic Stability was measured by placing 1g of water, 1g, of the orthosilicate ester under test and 9g of a commercially supplied glycol-ether hydraulic fluid base stock in a boiling tube, together with anti-bumping granules, and heating the mixture over a bunsen burner until it boiled, whereafter the boiling tube and contents were allowed to cool. The test mixture was observed during boiling and subsequent cooling for visual signs of hydrolytic instability such as gelling of the mixture or formation of a sediment and the orthosilicate ester was assigned a merit rating, based on the obervations, according to the scale:

| 0 test mixture gelled | 3 small sediment formed |
|---|---|
| 1 heavy sediment formed | 4 very slight sediment formed |
| 2 sediment formed | 5 clear |

The glycol-ether base stock used in these tests was a 550° F boiling point mixed ethylene/propylene glycol ether fluid partially inhibited with additives believed to be sodium nitrite, Agerite Resin D and benzotriazole. This was selected after preliminary tests in which the orthosilicate ester was boiled (a) with water, and (b) with water and glycol ether base stock containing no additives. These preliminary tests were found to be not sufficiently severe to evaluate the hydrolytic stability of the orthosilicate esters under test. The presence of the additives was found to increase deposit formation.

The results of Boiling Point determination, Hydrolytic Stability tests and Rubber Swell tests on styrene butadiene rubber and natural rubber are shown in the following Table 1. The results of Rubber Swell tests on nitrile rubber and chloroprene rubber are shown in the following Tables 2 and 3 respectively.

From the results set out in the Tables it is seen that the tested orthosilicate esters have satisfactory Boiling Points and superior Hydrolytic Stability. In addition low Rubber Swell values for nitrile and chloroprene rubbers were obtained. Rubber Swell values for styrene-butadiene and natural rubbers were high but the low chloroprene and nitrile values were considered to be of much greater importance in order to obtain fluids compatible with all these rubbers. When the orthosilicate esters are blended with known automotive hydraulic fluid base stocks (which are very poor with respect to chloroprene and nitrile but good with respect to styrene-butadiene and natural rubber) the Rubber Swell values of the blended fluid in comparison with the values of the orthosilicate ester will be lower in the case of styrene-butadiene and natural rubbers but higher in the case of nitrile and chloroprene rubbers.

In the following Tables 1 to 3 silicates A to C were glycol monoether orthosilicates not in accordance with the present invention, but prepared in the same manner as in Examples 1 to 12. Silicate A was tris(triethylene glycol monomethyl ether) i-butyl silicate which was analysed as containing 5.0% by weight Si (theory 4.7%). Silicate B was tetra (triethylene glycol monomethyl ether) silicate containing 3.77% by weight Si (theory 4.1%). Silicate C was bis (tripropylene glycol monomethyl ether) bis (triethylene glycol monomethyl ether) silicate containing 4.17% by weight Si (theory 3.78%).

Table 1

| Orthosilicate Tested | Boiling Point (° C) | Hydrolytic Stability Rating | 3-day Rubber Swell Tests (% Swell) | |
|---|---|---|---|---|
| | | | Styrene butadiene Rubber | Natural Rubber |
| Tris(triethylene glycol monomethyl ether) t-butyl silicate | 290 | 3 | 0.5 | 3.9 |
| Tris(tripropylene glycol monomethyl ether) neopentyl silicate | * | 3 | 34.2 | 23.7 |
| Tetra(tripropylene glycol monomethyl ether) silicate | * | 3 | 23.5 | 12.5 |
| Bis(dipropylene glycol monomethyl ether) bis (t-butyl) silicate | * | 4 | 51.7 | 55.5 |
| Bis(t-butyl)(dipropylene glycol monomethyl other)(triethylene glycol monomethyl ether) silicate | * | 4 | 51.2 | 41.8 |
| Tris(dipropylene glycol monomethyl ether) t-butyl silicate | 309 | 4 | 47.1 | 36.5 |
| Bis(triethylene glycol monomethyl ether) bis (t-butyl) silicate | 303 | 5 | 44.4 | 19.2 |
| Bis(tripropylene glycol monomethyl ether) bis (t-butyl) silicate | 226 | 5 | 39.9 | 44.1 |
| Tris(tripropylene glycol monomethyl ether) t-butyl silicate | 253 | 5 | 60.9 | 37.6 |
| Silicate A | 308 | 0 | 9.3 | 5.5 |
| Silicate B | 310 | 1 | 2.4 | −0.7 |
| Silicate C | 282 | 1 | 14.2 | 8.0 |

* Not measured

Table 2

| Orthosilicate Tested | 3-day Rubber Swell Test on Nitrile Rubber (%Swell) |
|---|---|
| Tetra(tripropylene glycol monomethyl ether) silicate | −2.4 |
| Bis(dipropylene glycol monomethyl ether) bis (t-butyl) silicate | 0 |
| Bis(t-butyl)(dipropylene glycol monomethyl ether)(triethylene glycol monomethyl ether) silicate | 2.6 |
| Tris(dipropylene glycol monomethyl ether) t-butyl silicate | −0.01 |
| Bis(triethylene glycol monomethyl ether bis t-butyl) silicate | 7.2 |
| Bis(tripropylene glycol monomethyl ether) bis (t-butyl) silicate | −0.34 |
| Silicate A | 20.8 |
| Silicate C | 6.5 |

Table 3

| Orthosilicate Tested | 3-day Rubber Swell Test on Chloroprene Rubber (% Swell) |
|---|---|
| Tris(triethylene glycol monomethyl ether) t-butyl silicate | 1.5 |
| Tris(tripropylene glycol monomethyl ether) neopentyl silicate | 0.2 |
| Silicate A | 17.4 |
| Silicate C | 11.3 |

We claim:

1. An orthosilicate ester having the general formula:

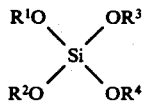

wherein $R^1$ is selected from the group consisting of propylene glycol monoalkyl ether residues containing from 1 to 2 carbon atoms in the terminal alkyl group and tertiary alkyl groups; each of $R^2$, $R^3$ and $R^4$ is the same or different and is selected from the group consisting of ethylene and propylene glycol monoalkyl ether residues containing from 1 to 2 carbon atoms in the terminal alkyl group and tertiary alkyl groups, provided that when $R^1$ is a propylene glycol monoalkyl ether residue each of $R^2$, $R^3$ and $R^4$ are also propylene glycol monoalkyl ether residues; the total number of carbon atoms in $R^1$, $R^2$, $R^3$ and $R^4$ being at least 15 and at least one of $R^1$, $R^2$, $R^3$, and $R^4$ being a glycol monoalkyl ether residue.

2. A compound according to claim 1 wherein the at least one glycol monoalkyl ether residue has the formula:

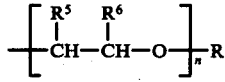

wherein each of $R_5$ and $R^6$ is selected from the group consisting of a hydrogen atom and a methyl group, provided that $R^5$ and $R^6$ are not both methyl groups; R is an alkyl group containing from 1 to 2 carbon atoms; and $n$ is an integer.

3. A compound according to claim 2 wherein $n$ is an integer of from 2 to 4.

4. A compound according to claim 1 wherein the total number of carbon atoms in $R^1$, $R^2$, $R^3$ and $R^4$ is from 15 to 60.

5. A compound according to claim 1 wherein at least one of the groups $R^1$, $R^2$, $R^3$ and $R^4$ is a tertiary alkyl group containing 4 to 8 carbon atoms.

6. An orthosilicate ester having the general formula:

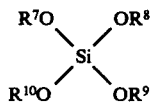

wherein,
i. each of $R^7$, $R^8$, $R^9$, and $R^{10}$ is the same or different; and
ii. each of $R^7$, $R^8$, $R^9$ and $R^{10}$ is a propylene glycol monoalkyl ether residue of the formula:

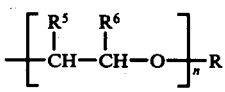

in which:

a. in each adjacent $R^5$ and $R^6$ one is a hydrogen atom and the other is a methyl group;
b. each $n$ is the same or different and the total value of all integers $n$ is from 8 to 16; and
c. each R is the same or different and is selected from the group consisting of a methyl group and an ethyl group.

7. A compound according to claim 6 wherein $R^7$, $R^8$, $R^9$ and $R^{10}$ are the same and each is selected from the group consisting of a tripropylene glycol monomethyl ether residue and a dipropylene glycol monomethyl ether residue.

8. An orthosilicate ester having the general formula:

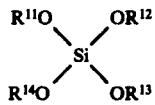

wherein,
i. $R^{11}$ is a tertiary alkyl group containing 4 to 8 carbon atoms;
ii. $R^{12}$ is a glycol monoalkyl ether residue of the formula:

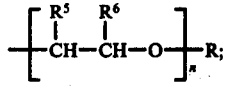

iii. $R^{13}$ is the same as or different from $R^{12}$ and is a glycol monoalkyl ether residue of the formula:

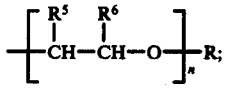

iv. $R^{14}$ is selected from the group consisting of tertiary alkyl groups containing 4 to 8 carbon atoms, being the same as or different from $R^{11}$, and glycol monoalkyl ether residues of the formula:

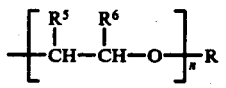

being the same as either $R^{12}$ or $R^{13}$ or being different from both $R^{12}$ and $R^{13}$; and
v. in glycol monoalkyl ether residues of the formula:

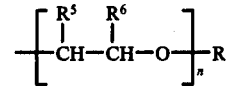

a. each $R^5$ and $R^6$ is the same or different and both are hydrogen atoms or in each adjacent $R^5$ and $R^6$ one is a hydrogen atom and the other is a methyl group;
b. each $n$ is the same or different and the total value of all integers $n$ is from 4 to 8 when $R^{14}$ is a branched chain alkyl group or from 6 to 12 when $R^{14}$ is a glycol monoalkyl ether residue; and
c. each R is the same or different and is selected from the group consisting of a methyl group and an ethyl group.

9. A compound according to claim 8 wherein $R^{11}$ is a t-butyl group and $R^{12}$, $R^{13}$ and $R^{14}$ are triethylene glycol monomethyl ether residues; $R^{11}$ is a neopentyl group and $R^{12}$, $R^{13}$ and $R^{14}$ are tripropylene glycol monomethyl ether residues; $R^{11}$ and $R^{14}$ are t-butyl groups and $R^{12}$ and $R^{13}$ are dipropylene glycol monomethyl ether residues; $R^{11}$ and $R^{14}$ are t-butyl groups, $R^{12}$ is a dipropylene glycol monomethyl ether residue and $R^{13}$ is a triethylene glycol monomethyl ether residue; $R^{11}$ is a t-butyl group and $R^{12}$, $R^{13}$ and $R^{14}$ are dipropylene glycol monomethyl ether residues; $R^{11}$ and $R^{14}$ are t-butyl groups and $R^{12}$ and $R^{13}$ are triethylene glycol monomethyl ether residues; $R^{11}$ and $R^{14}$ are t-butyl groups and $R^{12}$ and $R^{13}$ are tripropylene glycol monomethyl ether residues; or $R^{11}$ is a t-butyl group and $R^{12}$, $R^{13}$ and $R^{14}$ are tripropylene glycol monomethyl ether residues.

10. A process comprising reacting a silicon tetrahalide or transesterifying a tetra (hydrocarbyl) silicate with a hydroxy compound to form a compound as defined in claim 1.

11. A hydraulic fluid containing at least one compound as defined in claim 1.

12. A hydraulic fluid according to claim 11 containing from 1 to 99% by weight of the compound.

13. A hydraulic fluid according to claim 11 containing at least one conventional hydraulic fluid additive and/or base stock.

* * * * *